(12) United States Patent
Jägle

(10) Patent No.: US 7,784,722 B2
(45) Date of Patent: Aug. 31, 2010

(54) STIRRING OR DISPERSING DEVICE

(75) Inventor: Peter Jägle, Ballrechten-Dottingen (DE)

(73) Assignee: IKA - Werke GmbH & Co. KG, Staufen (DE)

( * ) Notice: Subject to any disclaimer, the term of this patent is extended or adjusted under 35 U.S.C. 154(b) by 368 days.

(21) Appl. No.: 11/919,442

(22) PCT Filed: Apr. 27, 2006

(86) PCT No.: PCT/EP2006/003920
§ 371 (c)(1),
(2), (4) Date: Oct. 26, 2007

(87) PCT Pub. No.: WO2006/117129
PCT Pub. Date: Nov. 9, 2006

(65) Prior Publication Data
US 2009/0294561 A1 Dec. 3, 2009

(30) Foreign Application Priority Data
Apr. 29, 2005 (DE) ........................ 10 2005 020 460

(51) Int. Cl.
B02C 17/16 (2006.01)
(52) U.S. Cl. ...................................... 241/172; 241/179
(58) Field of Classification Search ................. 241/172, 241/175, 179
See application file for complete search history.

(56) References Cited

U.S. PATENT DOCUMENTS

| 3,636,753 A | 1/1972 | Thiele et al. ................... 73/59 |
| 2002/0119200 A1 | 8/2002 | Haskell ....................... 424/489 |
| 2005/0023386 A1 | 2/2005 | Haskell ....................... 241/16 |

FOREIGN PATENT DOCUMENTS

| DE | 1 557 186 | 3/1972 |
| DE | 2 118 897 | 11/1972 |
| DE | 24 40 079 | 3/1975 |
| DE | 197 05 118 A1 | 8/1998 |
| EP | 0 409 039 A1 | 1/1991 |
| FR | 2 289 094 | 10/1975 |
| GB | 1 464 733 | 2/1977 |

Primary Examiner—Mark Rosenbaum
(74) Attorney, Agent, or Firm—K&L Gates, LLP

(57) ABSTRACT

A stirring or dispersing device (1), has a hermetically sealed mixing chamber (5), a tool (2), and a drive mechanism (4) located outside of the mixing chamber (5). The tool (2) can be driven around a central shaft in the mixing chamber (5) which has a rod-shaped element (3) for force transmission from the drive mechanism (4) to the tool (2). The rod-shaped element (3) is connected at the entry to the mixing chamber (5) with a diaphragm (6), which is a part of the wall (7) of the mixing chamber (5), and the rod-shaped element (3) can be put into a wobbling movement by the drive mechanism (4), so that its end located in the interior of the mixing chamber (5) performs a rotating movement. The tool is constituted by a number of grinding elements (22) or balls to be introduced into the mixing chamber (5).

18 Claims, 4 Drawing Sheets

STIRRING OR DISPERSING DEVICE

CROSS-REFERENCES TO RELATED APPLICATIONS

This application claims the benefit of German patent application DE 10 2005 020 460.0, filed Apr. 29, 2005, herein incorporated by reference.

BACKGROUND OF THE DISCLOSURE

The invention relates to a stirring or dispersing device, having a hermetically sealed mixing chamber, a dispersing tool, which can be driven around a central shaft in this mixing chamber and which has a rod-shaped element for force transmission from a drive mechanism to this tool, and having such a drive mechanism located outside of the mixing chamber, wherein the rod-shaped element is connected at the entry to the mixing chamber with a diaphragm which is a part of the wall of the mixing chamber, and the rod-shaped element can be put into a wobbling movement by the drive mechanism, so that its end located in the interior of the mixing chamber performs a rotating movement.

Stirring or mixing devices are already known in the prior art, for example from German Patent Publications DE-A-1 557 186 or DE-A-2 440 079, in which rod-shaped elements are connected at the entry to a mixing chamber with a diaphragm, and the respective rod-shaped element performs a wobbling movement by means of the transmission of a force from a drive mechanism connected with it. However, in these devices the stirring and mixing tool is connected with the rod-shaped element, so that it must also perform the wobbling movement of the rod-shaped element. Because of this, these devices can only be operated at low numbers of revolutions, thus can stir and mix the respective material, but possibly with only an unsatisfactory result. Moreover, imbalances can occur in these devices in the course of transmission of a force, and furthermore the devices require a large space because of the wobbling and rotating tool.

SUMMARY OF THE INVENTION

Therefore the object arises of further developing a device of the type defined at the outset in such a way that a good stirring and mixing result is achieved, along with reduced space requirements of the device.

For attaining this object it has been provided that the tool is constituted by a number of grinding elements or balls to be introduced into the mixing chamber. Here, the rotary movement of the drive mechanism is initially transformed into a wobbling movement of the rod-shaped element, whose end located in the mixing chamber performs a rotating movement. In turn, this movement in the mixing chamber leads to the material to be mixed, and the grinding elements are taken along as well by the end of the rod-shaped element and are set into motion. In the course of this movement a multitude of collisions between the grinding elements occurs and therefore, besides this mixing of the contents of the mixing chamber, possibly also the desired comminution or break-up of the material to be mixed, or its dispersion, given the correspondingly high rotating speed of the drive mechanism. By means of the seating of the rod-shaped element against the diaphragm and of the wobbling movement performed by the latter it is possible to realize a mixing chamber with considerably reduced space requirements, into which the material to be mixed is to be placed. The rod-shaped element moves in a wobbling manner with a defined deflection in this mixing chamber, which is a function of the flexibility of the diaphragm, and sets the grinding elements or balls, as well as the material to be mixed itself, into motion.

Because of its deflection, the diaphragm makes possible the movement of the rod-shaped element with the latter having to rotate around its own axis, for which reason it is not necessary to provide sealing rings or similar sealing elements in the area of the entry of this rod-shaped element into the mixing chamber, which therefore cannot become leaky. Instead, in spite of the introduction of a drive element, a hermetically sealed mixing chamber results, in which nevertheless the tool can be mechanically put into rotation by means of this drive element.

In another further development of the stirring or dispersing device, the rod-shaped element, which is arranged on both sides of the diaphragm, is supported by the diaphragm in a useful manner.

In another development of the stirring or dispersing device the desired transmission and conversion of the rotating movement of the drive mechanism can be realized in a particularly simple manner, wherein the end of the rod-shaped element facing the drive mechanism loosely engages an eccentric area of the rotating portion of the drive mechanism, and in this case the wobbling movement of the rod-shaped element occurs in that it is being taken along by a means of the drive mechanism provided for this.

A preferred further embodiment of the dispersing device therefore can consist in the drive mechanism having a pin, which rotates around its transverse shaft which is coaxial with the drive shaft and which rests against the end of the rod-shaped element on the side of the drive mechanism and thus sets the rod-shaped element into a wobbling movement.

In connection with an embodiment of the stirring or dispersing device, the rod-shaped elements is embodied in one piece with the diaphragm in an especially useful manner. However, other useful further developments of the connection of the rod-shaped element with the diaphragm as a part of the wall of the mixing chamber are also conceivable. For example, this connection between the rod and the diaphragm can be embodied in a hermetically sealed and force-transmitting manner by means of a chemical reaction between the materials of which the two parts are constituted. Also acceptable is a further development, in which the two parts enter into a one-piece connection by means of a two-component injection process. It is, however, furthermore conceivable to glue the diaphragm and the rod together, or to provide the rod with flanges on two sides, which are glued together, welded together or chemically connected on both sides with the diaphragm. Anyway, all the above mentioned measures are suitable for assuring the hermetic seal of the diaphragm. Furthermore, a clamped connection at an appropriately high clamping force between the rod-shaped element and the diaphragm is also possible in addition.

For example, the diaphragm can be fixed in place on the wall as a part of this wall by a clamped connection by means of a clamping piece. Useful further developments of the fastening of the diaphragm to the respective wall can consist in connecting the diaphragm, if desired together with the rod-shaped element, with the remainder of the wall by injection molding, gluing, welding or connections of this type directly and without additional means, such as the above mentioned clamping piece.

Another advantageous embodiment represents a stirring or dispersing device, in which the rod-shaped element is embodied to have several parts, in particular one part on each side of the diaphragm. It is then possible to provide rod-shaped elements of different linear measurements, which can be arranged later on the diaphragm, so that in this way mixing chambers of different linear extensions, and therefore also different volumes, if desired with an unchanged cross section, can be realized.

Particularly cost-effective embodiments of the stirring or dispersing device in accordance with the invention ensue if the rod-shaped element is designed to be rectilinear or to extend rectilinearly. However, different embodiments of the rod geometry are also conceivable, furthermore, additional elements aiding the respective work process can be arranged on the rod-shaped element, for example a fin or similar eccentric element.

Depending on the purpose of use of the stirring or dispensing device, a user would like to affect various parameters of the desired work process in order to arrive at an optimal result. Thus, for example, in a process in which the material to be mixed is comminuted, possibly only a few grinding elements will be employed at high speed while, if the material to be mixed is to be pulverized, more grinding elements will be employed at a lower speed. Since here the size and material of the grinding elements play a role, it can be provided in a useful embodiment of the stirring or dispersing device in accordance with the invention for the grinding elements to be of different sizes, for example between 0.25 mm and 8 mm, and/or to be made of different materials, for example of glass or a metallic or ceramic material. It is possible for the user to individually select a fill level of the mixing chamber with grinding elements, together with the driving speed, oriented to the desired result.

It is advantageously possible in a different embodiment of the stirring or dispersing device to provide a releasable cover on the mixing chamber, which can be removed for introducing the material to be mixed, as well as for exchanging the tool. It is not absolutely necessary here to remove the cover completely, instead, so as not to be lost, it can be provided with any type of an additional connecting element, for example a loss-preventing securing device or the like at the exterior wall of the mixing chamber.

The cover in particular, but also a different wall of the mixing chamber of the stirring or dispersing device, can contain a diaphragm which can be pierced, through which, with the aid of a hollow needle or a syringe, the material to be mixed, or constituents to be added or mixed in, can be introduced into the mixing chamber or removed therefrom. In particular in the case in which the device is indeed only used once and is thereafter recycled, and wherein removal is actually only performed by means of a hollow needle, the diaphragm supporting the rod-shaped element can already be provided as the diaphragm which can be pierced, so that it is possible to forego the arrangement of a further diaphragm. The simultaneous provision of several diaphragms as diaphragms which can be pierced is of course possible.

Furthermore, in a further development of the stirring or dispersing device in accordance with the invention, for achieving an even better mixing and dispersing result it is usefully possible to provide protrusions, ribs or similar devices which break the flow at the axis-parallel wall, at least in some areas, which aid the corresponding process. At the same time these devices can be used in turn for fixing still further elements in place for aiding the work process.

BRIEF DESCRIPTION OF THE DRAWINGS

The invention will be explained in greater detail in what follows by means of exemplary embodiments shown in the drawings. Shown are in.

DETAILED DESCRIPTION OF THE PREFERRED EMBODIMENT

Figure 1:
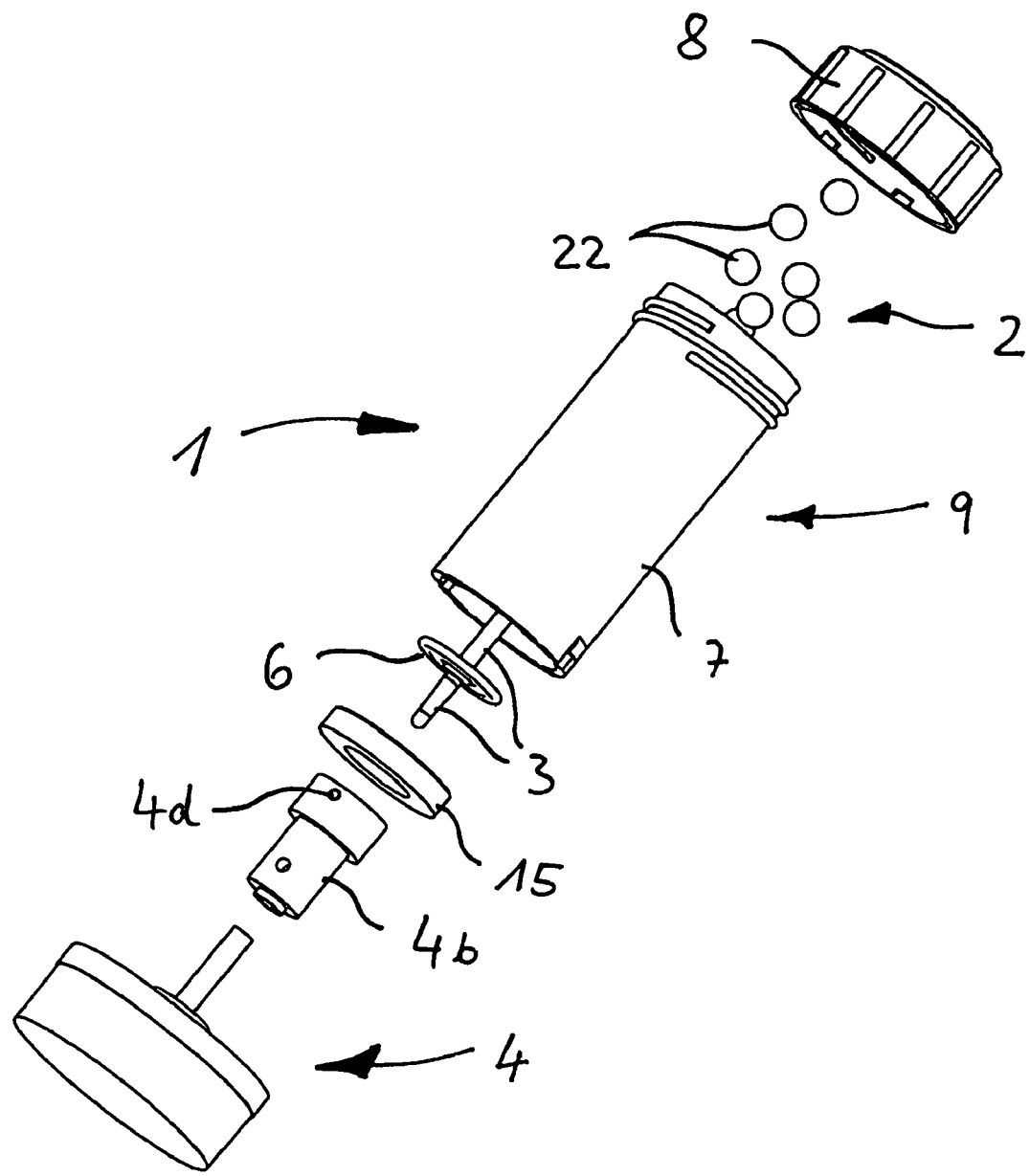
FIG. 1, a first embodiment of a stirring or dispersing device in an exploded view, FIG. 2, a longitudinal section through a lateral view of the stirring or dispensing device in FIG. 1 in the assembled state and in a vertical position with a drive mechanism at the bottom, FIG. 3, a longitudinal section through a lateral view of another stirring or dispensing device, namely with the drive mechanism arranged on top, and FIGS. 4 and 5, two front views in cross section of an embodiment of the stirring or dispersing device with the rod-shaped element and grinding elements in the mixing chamber.

FIG. 1 shows a stirring or dispersing unit, identified as a whole by 1, having an essentially cylindrical tube-shaped body 9, in whose interior a hermetically sealed mixing chamber 5, not visible here, is formed. A stirring or dispersing tool 2, which can be driven around a central shaft, to which a force from a drive mechanism 4 is transmitted by means of a rod-shaped element 3, is located in this mixing chamber 5. The drive mechanism 4 with a coupling 4b is located outside of the mixing chamber 5 at the lower end of the stirring or dispersing device 1, which can be plugged on the drive mechanism 4 and can be fixed in place on the body 9 in this area of the stirring or dispersing device 1 by fixation aids in the form of quarter-turn fasteners. It can also be seen in FIG. 1 that the rod-shaped element 3 is connected with the diaphragm 6 at the entry into the mixing chamber 5. The rod-shaped element 3, together with the diaphragm 6, is fixed in place at the entry to the mixing chamber 5 by a ring-shaped closure element 15, so that the diaphragm 6 constitutes a portion of the wall 7 of the mixing chamber 5, whose remaining portion is constituted by the walls of the cylindrical body and by the cover 8 located at the end facing away from the drive mechanism 4. The rod-shaped element 3 is set into a wobbling motion by the drive mechanism 4, then its end located in the mixing chamber the performs a rotating movement, wherein the diaphragm 6 participates in this movement by a kneading movement, which deforms it in a defined manner. The tool 2, which is constituted by grinding elements 22 in the form of balls, is also set in motion by this, wherein the action of the rod-shaped element 3 against the tool 2 takes place eccentrically in regard to its axis of rotation, and the rod-shaped element 3 is supported by the diaphragm 6.

For closing the cylindrical body 9, and therefore also of the mixing chamber 5, a cover 8 with a diaphragm 6 which can be pierced and is not visible in this view, is provided, which can be attached to the end of the bottom 9 facing away from the drive mechanism with the aid of a screw thread located on the exterior of the body 9.

Figure 2:
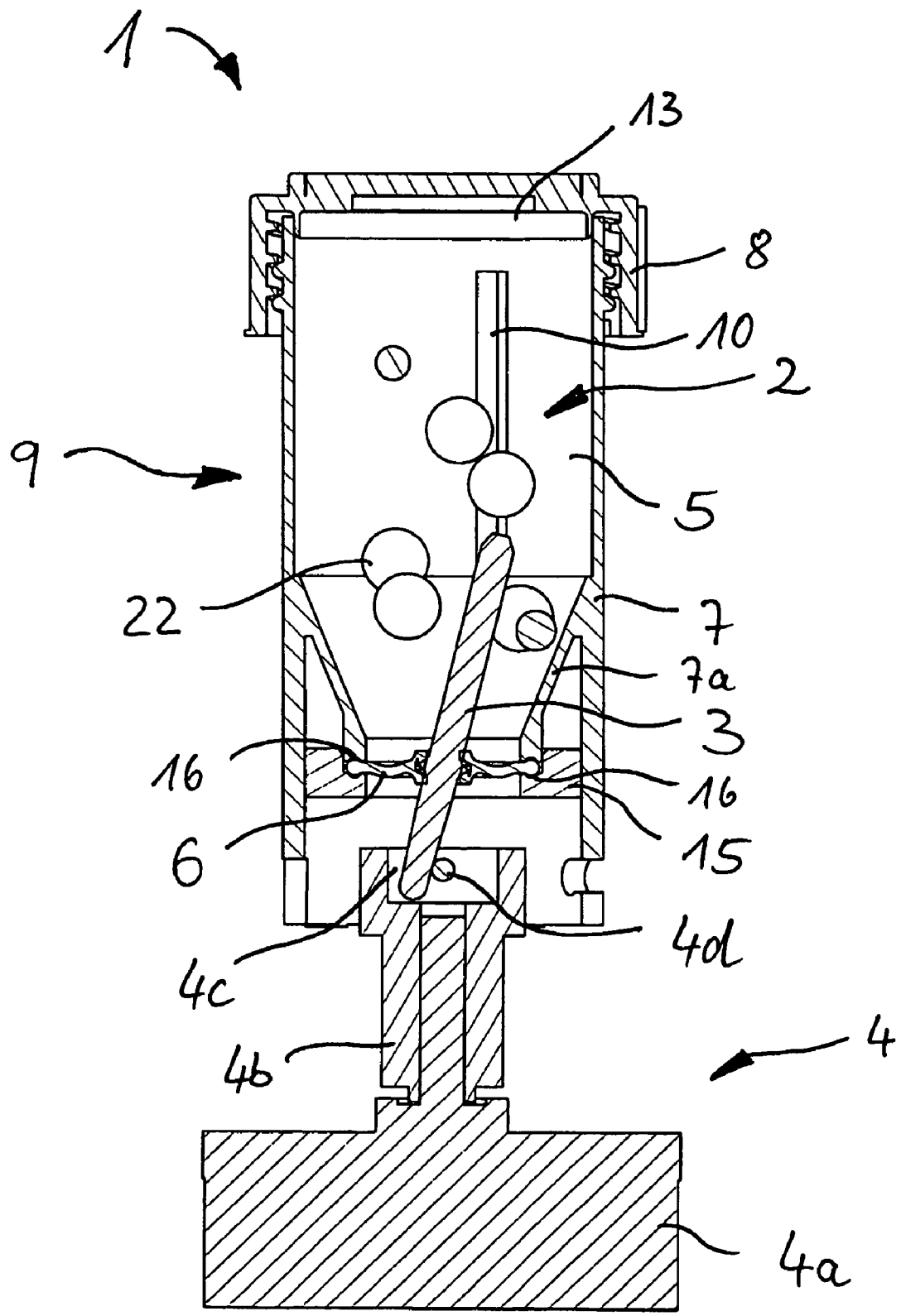

The stirring or dispersing device 1 can be seen in FIG. 2 in the assembled state and placed on the drive mechanism 4 standing on a not further represented base. Here, the drive mechanism 4 has a motor 4a with a coupling 4b axially fixed in place on the motor shaft, which drives the rod-shaped element 3 which, together with the diaphragm 6, constitutes a unit, by means of a rotatory motion. This occurs in that the end facing the drive mechanism 4 of the rod-shaped element 3 made in one piece with the diaphragm 6, loosely and eccentrically engages a space 4c of the coupling 4b, where it is taken along by a pin 4d, which extends vertically in respect to the axis of rotation and rests against the surface of the rod-shaped element 3. When driven, the pin 4d rotates around its transverse axis, which in turn is coaxial with the drive shaft. The position of this pin 4d and its diameter determine the diameter of the circular movement of the ends of the rod-shaped element 3, or its angle in respect to the drive shaft. The eccentric engagement of the end of the rod-shaped element 3 facing the drive mechanism 4 results in its other end facing the tool 2 also engaging the mixing chamber 5 eccentrically.

When driven, the ends of the rod-shaped element 3 seated so they extend through the diaphragm 6 perform a circular movement so that the stirring or dispersing tool 2, here in the form of balls of different size as grinding elements 22, at the end of the rod-shaped element 3 facing away from the drive mechanism 4, is also driven. These grinding elements 22 are kept loosely in the mixing chamber 5 and move together with the material to be stirred, mixed or dispersed, not represented in detail, because of the motion of the end of the rod-shaped element 3 entering between them.

The deflection of the diaphragm 6 as a result of the circular movement of the ends of the wobbling, rectilinearly embodied rod-shaped element 3, which can also be seen in FIG. 2, makes it clear that it is subjected to a kneading action when it is operated, which causes just this deflection or deformation. In this case the diaphragm 6 is fixed in place on the inner edge of the wall 7 and, in regard to the free end of the wall-like border 7a of the mixing chamber 5 which terminates conically in the mixing chamber 7, by clamping by means of the ring-shaped closure element 15, wherein groove-like indentations 16, which respectively run around the opposing ends of the border 7a and the closure element 15, are provided for receiving the thickened edge of the diaphragm 6.

It can furthermore be seen that a rib with a cutting edge is arranged in the interior of the mixing chamber and extends along the axis-parallel wall 7 as a flow-breaking device 10, while fastening or snap-in means, which can be arranged between the closure element 15 and the mixing chamber border, are not shown in detail.

At its end facing away from the drive mechanism 4, the device 1 is provided with a cover 8, which is screwed onto it over an exterior screw thread on the body 9 and in this way closes the respective end of the mixing chamber. At its front, the cover 8 is provided with a diaphragm 13, which can be pierced so that, following removal from the drive mechanism 4, the material to be mixed in the mixing chamber 5 is accessible from both ends by piercing through the respective diaphragm 6, 13, but can also be removed from the mixing chamber by opening the cover 8.

Figure 3:
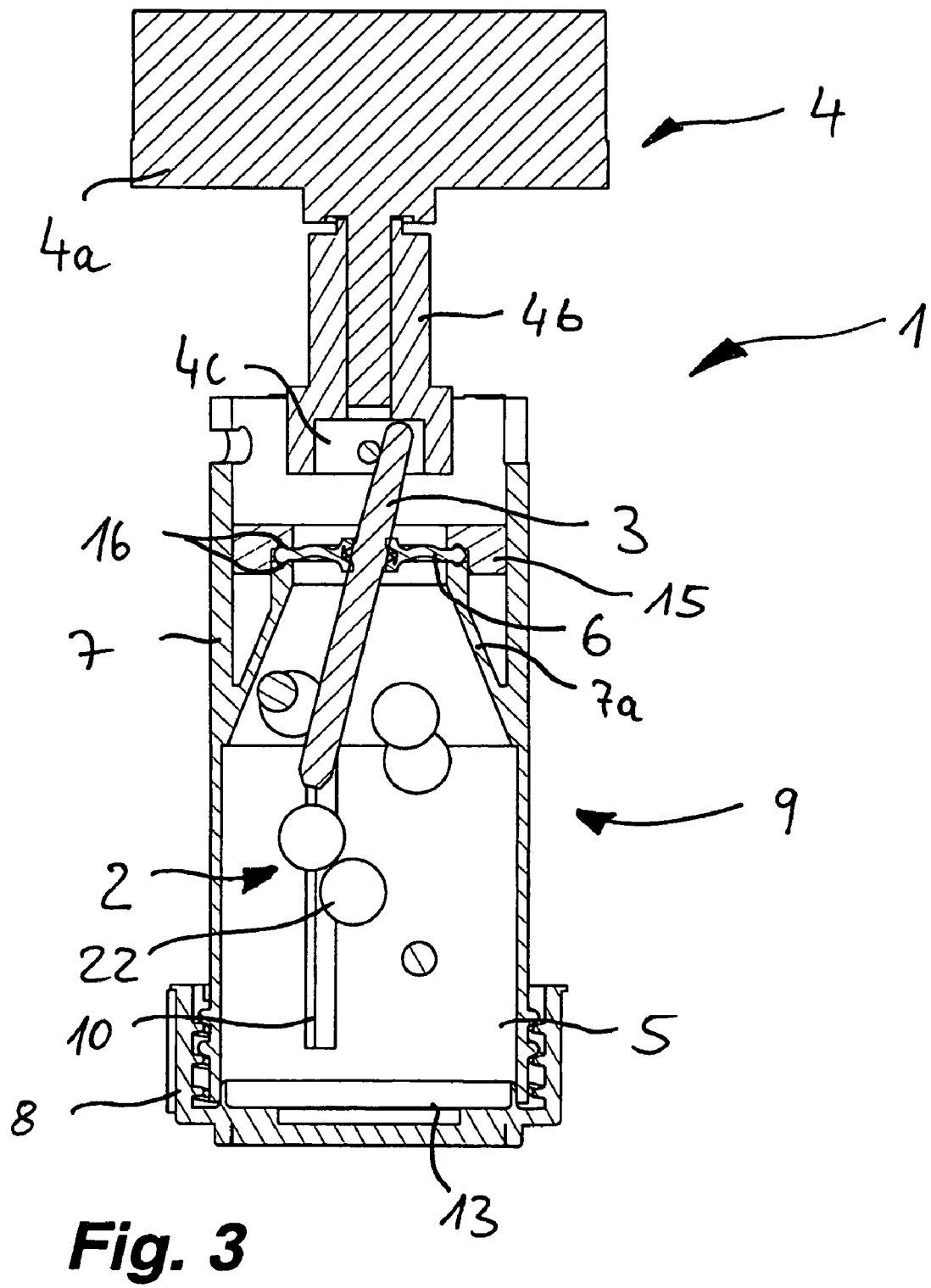

FIG. 3 shows an embodiment of the stirring or dispersing device 1 which in its essential parts corresponds to that in FIG. 2 but, although it is placed on the cover 8 in the same vertical position, the drive mechanism 4 of the device 1 is introduced from above. Here, too, the taking-along of the rod-shaped element 3 takes place by means of a pin 4d, which is arranged perpendicularly in respect to the axis of rotation of the drive mechanism 4, against which the end of the rod-shaped element facing the drive mechanism and located outside of the mixing chamber 5 rests. In this case, while deflecting the diaphragm 6 inside the mixing chamber 5, it engages with its respective end the grinding elements 22 of the stirring or dispersing tool 2 from the top to the bottom and sets them also into motion by means of its own rotating movement.

In this case the cover 8 with the diaphragm 13, which can be pierced, arranged thereon, and which covers and closes a front access opening of the cover 8, constitutes the lower termination of the stirring or dispersing device 1 and its support surface at the same time.

Figure 4:
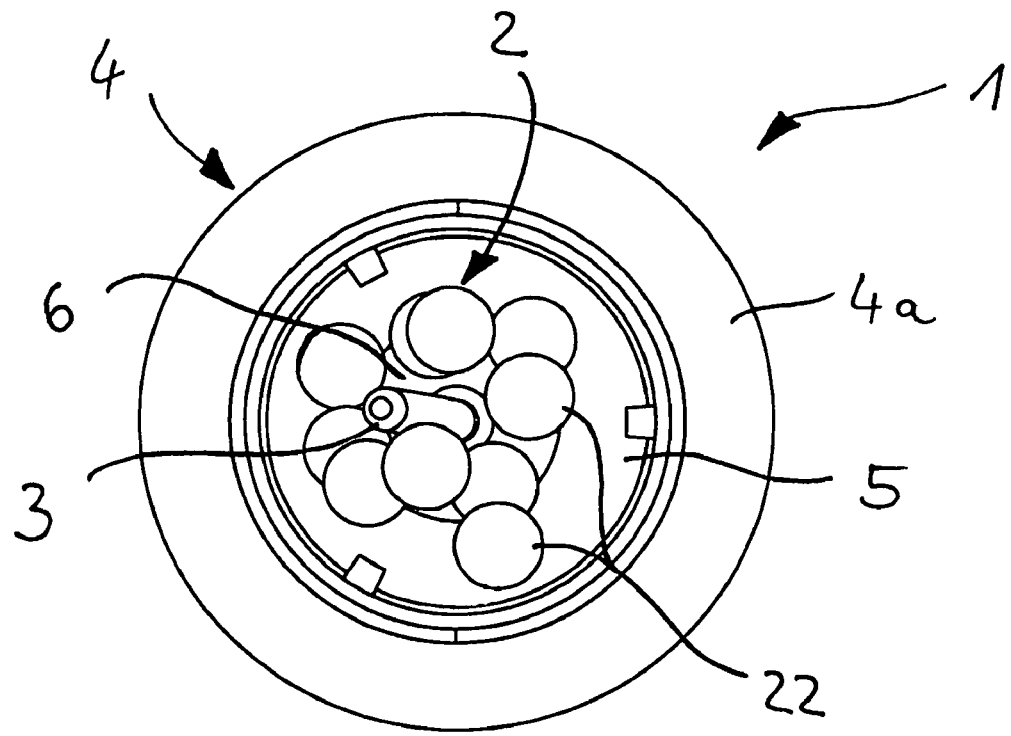
Figure 5:
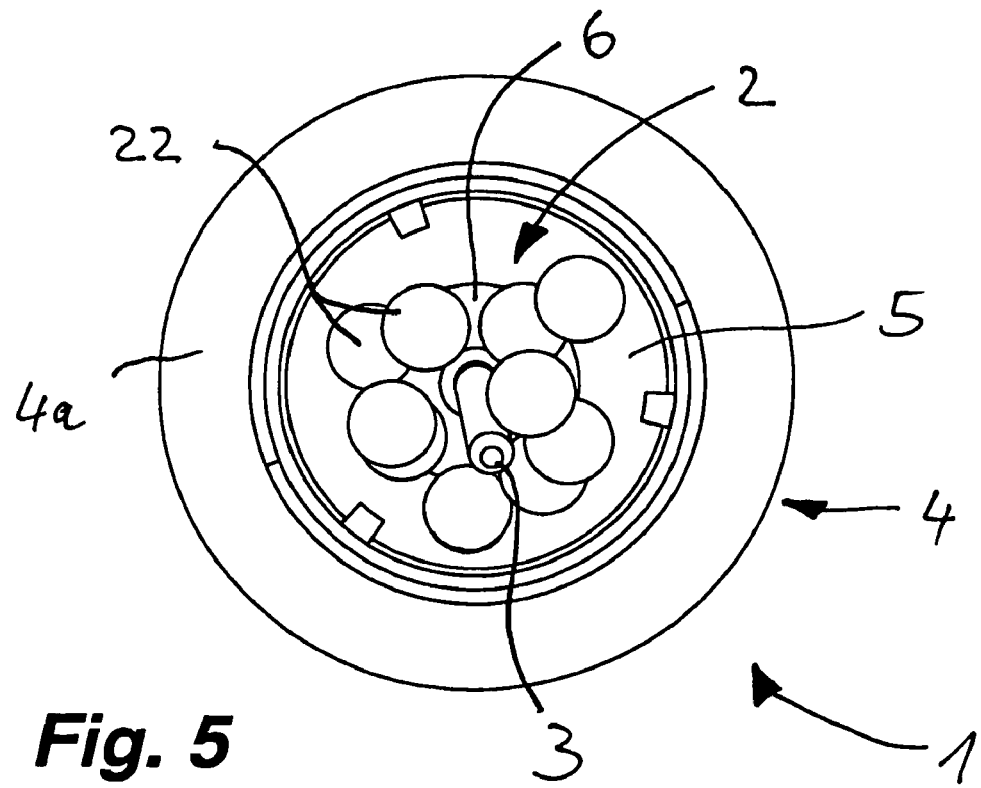

FIGS. 4 and 5 show front plan views of the stirring or dispersing device 1 placed on top of the drive mechanism 4 from the direction of the removed cover 8, with two different positions of the rod-shaped element 3 which is in motion, has a substantially round cross section, as well as rounded-off ends, and which enters into the stirring or dispersion tool 2 in the form of the grinding elements 22 loosely contained in the mixing chamber 5. The end of the rod-shaped element 3 entering into the mixing chamber 5 is furthermore flattened at its tip. Because of the eccentric engagement, which also deflects the diaphragm 6, of the end of the rod-shaped element 3 facing the drive mechanism 4 with the pin 4d, not visible, the end of the rod-shaped element 3 inside the mixing chamber 5 also engages the tool 2 eccentrically in respect to the drive shaft.

Thus, the above described invention relates to a stirring or dispersing device 1, having a hermetically sealed mixing chamber 5, a tool 2, which can be driven around a central shaft in this mixing chamber 5 and has a rod-shaped element 3 for force transmission from a drive mechanism 4 to this tool 2, and having such a drive mechanism 4 located outside of the mixing chamber 5, wherein the rod-shaped element 3 is connected at the entry to the mixing chamber 5 with a diaphragm 6, which is a part of the wall 7 of the mixing chamber 5, and the rod-shaped element 3 can be put into a wobbling movement by the drive mechanism 4, so that its end located in the interior of the mixing chamber 5 performs a rotating movement.

In order to achieve an optimal stirring, dispersing, grinding and comminution effect by simple means, the stirring or dispersing device 1 has been provided in such a way, that the tool 2 is constituted by a number of grinding elements 22 or balls to be introduced into the mixing chamber 5.

The invention claimed is:

1. A stirring or dispersing device (1), having a hermetically sealed mixing chamber (5), a tool (2), and a drive mechanism (4) located outside of the mixing chamber (5), wherein the tool (2) can be driven around a central shaft in the mixing chamber (5) and has a rod-shaped element (3) for force transmission from the drive mechanism (4) to the tool (2), wherein the rod-shaped element (3) is connected at the entry to the mixing chamber (5) with a diaphragm (6), which is a part of a wall (7) of the mixing chamber (5), and wherein the rod-shaped element (3) can be put into a wobbling movement by the drive mechanism (4), so that its end located in the interior of the mixing chamber (5) performs a rotating movement, characterized in that the tool comprises a number of grinding elements (22) or balls to be introduced into the mixing chamber (5) and wherein the stirring or dispersing device is further characterized in that, with its end facing the drive mechanism (4), the rod-shaped element (3) loosely engages an eccentric area of the rotating portion of the drive mechanism (4).

2. The stirring or dispersing device in accordance with claim 1, characterized in that the diaphragm (6) supports the rod-shaped element (3).

3. The stirring or dispersing device in accordance with claim 1, characterized in that the drive mechanism (4) has a pin (4d), which rotates around its transverse axis which is coaxial with the drive shaft, and which rests against the end on the side of the rod-shaped element (3) toward the drive mechanism.

4. The stirring or dispersing device in accordance with claim 1, characterized in that the rod-shaped element (3) is embodied in one piece with the diaphragm (6).

5. The stirring or dispersing device in accordance with claim 1, characterized in that the rod-shaped element (3) and the diaphragm (6) are connected by means of a chemical reaction between their materials.

6. The stirring or dispersing device in accordance with claim 1, characterized in that the rod-shaped element (3) is connected with the diaphragm (6) by means of an adhesive, a flanged connection, a welded connection or a clamped connection.

7. The stirring or dispersing device in accordance with claim 1, characterized in that the diaphragm (6), optionally together with the rod-shaped element (3), is connected with the remaining wall (7).

8. The stirring or dispersing device in accordance with claim 7, wherein the diaphragm (6) is connected with the remaining wall (7) by means of injection molding, gluing, or welding.

9. The stirring or dispersing device in accordance with claim 1, characterized in that the rod-shaped element (3) is embodied to have several parts.

10. The stirring or dispersing device in accordance with claim 9, wherein the several parts includes at least one part on each side of the diaphragm (6).

11. The stirring or dispersing device in accordance with claim 1, characterized in that the rod-shaped element (3) is designed to be rectilinear.

12. The stirring or dispersing device in accordance with claim 1, characterized in that the grinding elements (22) are of different sizes or are made of different materials.

13. The stirring or dispersing device in accordance with claim 12, wherein the grinding elements (22) are made of a glass, a metallic or a ceramic material.

14. The stirring or dispersing device in accordance with claim 1, characterized in that a releasable cover (8) is provided on the mixing chamber (5).

15. The stirring or dispersing device in accordance with claim 1, characterized in that a diaphragm (13), which can be pierced, is provided in one of the walls (7).

16. The stirring or dispersing device in accordance with claim 15, wherein the diaphragm (13), which can be pierced, is provided in the cover (8) of the mixing chamber.

17. The stirring or dispersing device in accordance with claim 1, characterized in that the diaphragm (6) supporting the rod-shaped element (3) is provided in the form of a diaphragm which can be pierced.

18. The stirring or dispersing device in accordance with claim 1, characterized in that protrusions, ribs or similar flow-interrupting devices (10) are provided, at least on portions of the axis-parallel wall (7).

* * * * *